(12) United States Patent
Loh et al.

(10) Patent No.: US 11,083,393 B2
(45) Date of Patent: Aug. 10, 2021

(54) NON-CONTACT TOMOGRAPHIC IMAGING AND THIN FILM SENSORS FOR SENSING PERMITTIVITY CHANGES

(71) Applicant: The Regents of the University of California, Oakland, CA (US)

(72) Inventors: Kenneth J. Loh, La Jolla, CA (US); Sumit Gupta, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 552 days.

(21) Appl. No.: 15/890,087

(22) Filed: Feb. 6, 2018

(65) Prior Publication Data

US 2018/0220920 A1  Aug. 9, 2018

Related U.S. Application Data (60) Provisional application No. 62/455,454, filed on Feb. 6, 2017.

(51) Int. Cl.
| | |
|---|---|
| A61B 5/05 | (2021.01) |
| A61B 5/0536 | (2021.01) |
| A61B 5/0531 | (2021.01) |
| G01L 1/14 | (2006.01) |
| G01N 27/22 | (2006.01) |

(52) U.S. Cl.
CPC .......... *A61B 5/0536* (2013.01); *A61B 5/0531* (2013.01); *G01L 1/146* (2013.01); *G01N 27/226* (2013.01)

(58) Field of Classification Search
CPC ..... A61B 5/0531; G01L 1/146; G01N 27/226
See application file for complete search history.

(56) References Cited

U.S. PATENT DOCUMENTS

| | | | | |
|---|---|---|---|---|
| 2004/0122790 A1* | 6/2004 | Walker | ................ | G16H 50/70 |
| 2009/0121727 A1* | 5/2009 | Lynch | ................ | G01R 27/02 |
| | | | | 324/609 |
| 2014/0365152 A1* | 12/2014 | Marashdeh | ........... | G01F 1/7046 |
| | | | | 702/65 |
| 2015/0044656 A1* | 2/2015 | Eichhorn | ................ | A61B 5/11 |
| | | | | 434/267 |
| 2015/0066415 A1* | 3/2015 | Hamilton | ............. | G01R 31/001 |
| | | | | 702/119 |
| 2016/0091448 A1* | 3/2016 | Soleimani | ............. | G01N 27/22 |
| | | | | 324/654 |
| 2016/0238547 A1* | 8/2016 | Park | ........................ | C08K 7/24 |
| 2017/0105648 A1* | 4/2017 | Boverman | ............. | A61B 5/053 |
| 2017/0323461 A1* | 11/2017 | Oeckl | .................... | G06T 11/006 |

* cited by examiner

*Primary Examiner* — Alvaro E Fortich
(74) *Attorney, Agent, or Firm* — Sheppard, Mullin, Richter & Hampton LLP (57) ABSTRACT

Systems and methods for monitoring a change to a region of interest over time are disclosed. Exemplary embodiments may: (a) apply one or more layers of a stress-sensitive material to an object of interest; (b) incorporate the object of interest into a region of interest; (c) insert the region of interest with stress-sensitive material into an electrical capacitance tomography (ECT) device to interrogate the region of interest; (d) generate a first map of the region of interest based on captured information from the ECT device; (e) after a first length of time, repeat steps (c)-(d) to generate a second map of the region of interest; and (f) compare the first map to the second map to determine changes to the region of interest based on changes to the stress-sensitive material.

14 Claims, 10 Drawing Sheets

NON-CONTACT TOMOGRAPHIC IMAGING AND THIN FILM SENSORS FOR SENSING PERMITTIVITY CHANGES

RELATED APPLICATIONS

This application claims the benefit of U.S. Provisional Patent Application No. 62/455,454, filed on Feb. 6, 2017, the contents of which are incorporated herein by reference in their entirety.

FUNDING

This research was funded by the Office of Naval Research (ONR) under contract no. N00014-17-2550. Partial support was also received from Jacobs School of Engineering, University of California, San Diego.

TECHNICAL FIELD

The disclosed technology relates generally to electrical capacitance tomography (ECT) imaging, and more particularly, several embodiments relate to systems and methods for non-contact, non-invasive monitoring of changes to a region of interest over time.

DESCRIPTION OF THE RELATED ART

ECT is a soft-field imaging technique that attempts to image the permittivity distribution of a predefined region. A series of boundary electrodes may be equidistantly arranged in a circular (or other-shaped) array at the boundary of the sensing area, where each of them are separately excited with an alternating current (AC) signal and the capacitance between the excitation and the other electrodes are measured. Electrical permittivity distribution inside that predefined sensing area can be reconstructed from this measured set of capacitances.

ECT may have been used for flow monitoring, monitoring industrial processes, or some biomedical imaging. Electrical impedance tomography (EIT) and ECT-based dual modality imaging techniques may be used to provide real time 3D images to navigate the surgery tools in the femoral bone during total hip replacement. Real time, volumetric capacitance-based imaging techniques may be used to monitor brain activities related to human motoric and lung functions.

Besides the aforementioned methods, different imaging techniques may be used for the diagnosis of infections at prosthetic joints. Magnetic resonance imaging (MRI) and computed tomography (CT) may be other imaging techniques, but these are sensitive to artifacts produced by prosthetic devices. CT imaging also requires radiation, which can be harmful at high doses. In addition, MRI requires patients be injected with harsh contrast agents. Radionuclide imaging is generally employed for imaging metallic implants. Additionally, combined leukocyte-marrow scintigraphy and F-fluoro-2-deoxyglucose positron emission tomography (FDG-PET) may also be used. However, combined leukocyte-marrow scintigraphy is time, labor, and cost intensive. Additionally, even the merit of FDG-PET imaging as a reliable prosthetic joint infection monitoring tool is still under debate.

SUMMARY

Embodiments of the systems and methods disclosed herein provide systems and methods for monitoring an object of interest. In various embodiments, a stress-sensitive material may be applied to an object of interest, which may be incorporated into a region of interest. The stress-sensitive material may change in a dielectric property as a function of stress. The region of interest may be interrogated using ECT. Data captured during the interrogation may be used to generate maps of the region of interest. The process may be repeated over time to generate subsequent maps. The maps may be compared to a first map, which may represent a baseline. Changes to a subsequent map compared to the first map may indicate successful or unsuccessful incorporation of the object of interest. The changes may otherwise indicate changes to the region of interest, the object of interest, or the stress-sensitive material. Using stress-sensitive material on an object of interest may provide a non-contact, non-invasive method of monitoring various structures.

In various embodiments, a first map of the region of interest may be generated by interrogating the region of interest using ECT. The region of interest may include an object of interest that has stress-sensitive material applied to the object of interest. The stress-sensitive material may change a dielectric property in response to changes in stress. The first map may represent a baseline of the region of interest. After a first length of time, a second map of the region of interest may be generated. The second map may be compared to the first map, the baseline. Changes between the second map and the first map may indicate unsuccessful incorporation of the object of interest into the region of interest, or the changes may indicate changes to other features in the region of interest. By providing a system that allows non-contact, non-invasive monitoring of various structures, objects of interest do not need to be dismantled from a region of interest in order to be inspected. Moreover, detailed maps of the changes to the region of interest may be generated. The amount of time and money spent investigating potential changes to regions of interest, such as osseointegrated prostheses or other structural components, may be reduced.

According to an embodiment of the disclosed technology, a method of monitoring a change to a region of interest over time comprises (a) applying layers of a stress-sensitive material to an object of interest; (b) incorporating the object of interest into a region of interest; (c) inserting the region of interest with stress-sensitive material into an electrical capacitance tomography (ECT) device to interrogate the region of interest; (d) generating a first map of the region of interest based on captured information from the ECT device; (e) after a first length of time, repeating steps (c)-(d) to generate a second map of the region of interest; and (f) comparing the first map to the second map to determine changes to the region of interest based on changes to the stress-sensitive material.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

The following description is not to be taken in a limiting sense, but is made merely for the purpose of describing the general principles of the disclosed embodiments. Numerous specific details are set forth to provide a full understanding of various aspects of the subject disclosure. It will be apparent, however, to one ordinarily skilled in the art that various aspects of the subject disclosure may be practiced without some of these specific details. In other instances, well-known structures and techniques have not been shown in detail to avoid unnecessarily obscuring the subject disclosure.

Embodiments of the apparatus and methods disclosed herein provide a non-contact, non-invasive technique for monitoring changes in properties of a region of interest. These changes may include, for example, changes in strain on the object of interest, changes in pH to the object of interest, or other stressors on, or around, the region of interest. This monitoring scheme may work in some embodiments by coupling an electrical capacitance tomography (ECT) device with stress-sensitive nanocomposite film (as an example) applied to an object of interest. The object of interest may be incorporated into a region of interest. For example, an object of interest may be a prosthetic or other implantable object, and a region of interest may be a prosthetic socket to accept a prosthetic limb after amputation. As another example, an object of interest may be an implanted hip, elbow, knee or other prosthetic, and the region of interest may be the surrounding tissue into which the prosthetic is implanted. As yet another example, the object of interest may be any other embeddable or implantable device with which the technology disclosed herein may be used. The object of interest may include part of prostheses, hulls, pipes, rods, bones, tissues, limbs, pins, sockets, or other structures.

ECT, or other like technologies, may use applied electrical excitations to obtain readings from the nanocomposite film applied to the object of interest. Measurements from these readings (e.g., measurements at the boundaries) may be used to reconstruct the spatial permittivity distribution inside the sensing region. The stress-sensitive nanocomposite may pronounce permittivity changes due to changes occurring at the object of interest, thereby enhancing detection sensitivity and resolution. A map, such as a spatial permittivity map, may be constructed from measuring the changes in properties (e.g., capacitance) over time to the object of interest. Constructed maps may be compared to a baseline map, prepared after the stress-sensitive nanocomposite film is applied to the object of interest. Changes to the maps may indicate successful incorporation or other changes to the region of interest.

Particularly, some embodiments may provide a non-contact, non-invasive system that determines changes in properties to a stress-sensitive film applied to an object of interest. The system can be configured to interrogate a region of interest with an electric field. A region of interest may include an object of interest, a stress-sensitive film, or other features. A stress-sensitive film may be applied to the object of interest. In one application, the object of interest may be a prosthesis attached to the remaining extremity of an amputated limb, which may be the region of interest. After initial application of the stress-sensitive film, the system may interrogate the prosthesis and the applied stress-sensitive film and capture information. The system may represent this information as a spatial map depicting electrical or dielectric properties such as, for example, permittivity, as a function of position. This initial map may form a baseline measurement that can be used to compare against subsequent maps captured in the future. Subsequent measurements can be made after the device has been in use, and these measurements may be used to create subsequent maps. Changes in the maps may reflect a change in the prosthesis in situ, such as, for example, infection, loosening of the prosthesis, or stresses on the prosthesis. Although embodiments of the systems and methods disclosed are described herein as using an ECT device for the measurement, various other imaging devices may be used to detect changes in various properties, such as electrical properties or dielectric properties. Various embodiments can be implemented to not only determine changes to an object of interest, but also to determine relative changes to a stress-sensitive film on an object of interest using a non-contact, non-invasive imaging system.

Figure 1:
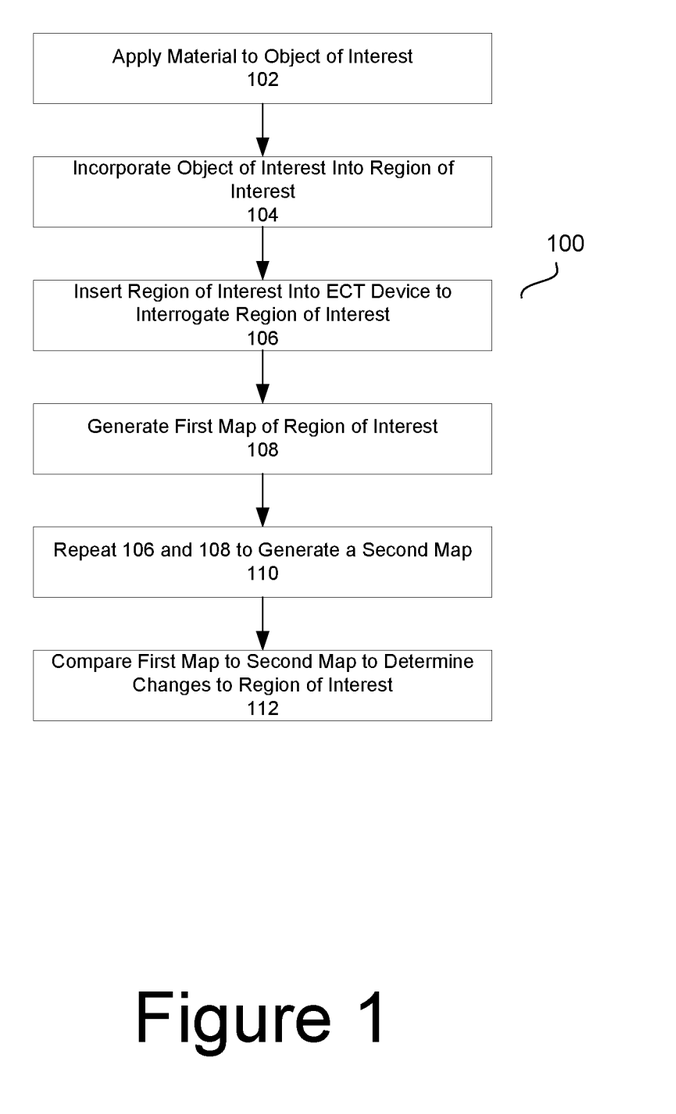
FIG. 1 is an operational flow diagram illustrating an example process for monitoring permittivity changes of an object of interest according to one particular embodiment.

FIG. 1 is an operational flow diagram illustrating an example process for monitoring permittivity changes of an object of interest according to one particular embodiment. At operation 102, a stress-sensitive material is applied to the object of interest. The stress-sensitive material applied may include a thin film, nanocomposite, or thin film sensors. The stress-sensitive material may be sensitive to pH, strain, magnetism, electricity, heat, liquid, vibrations, or other stressors. The stress-sensitive material may react to the stressors as a function of a property, such as a dielectric property. In some embodiments, the property may be another property, such as a magnetic property, a gravitational property, or other properties.

Figure 3A:
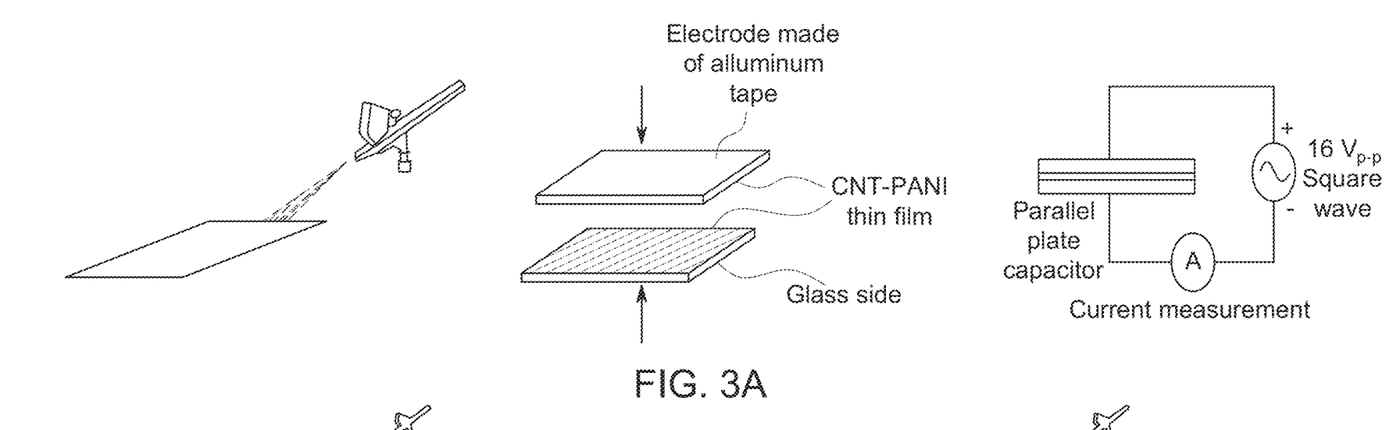
FIG. 3A illustrates a spray coated film arranged to form a parallel-plate capacitor according to one particular embodiment.
Figure 3B:
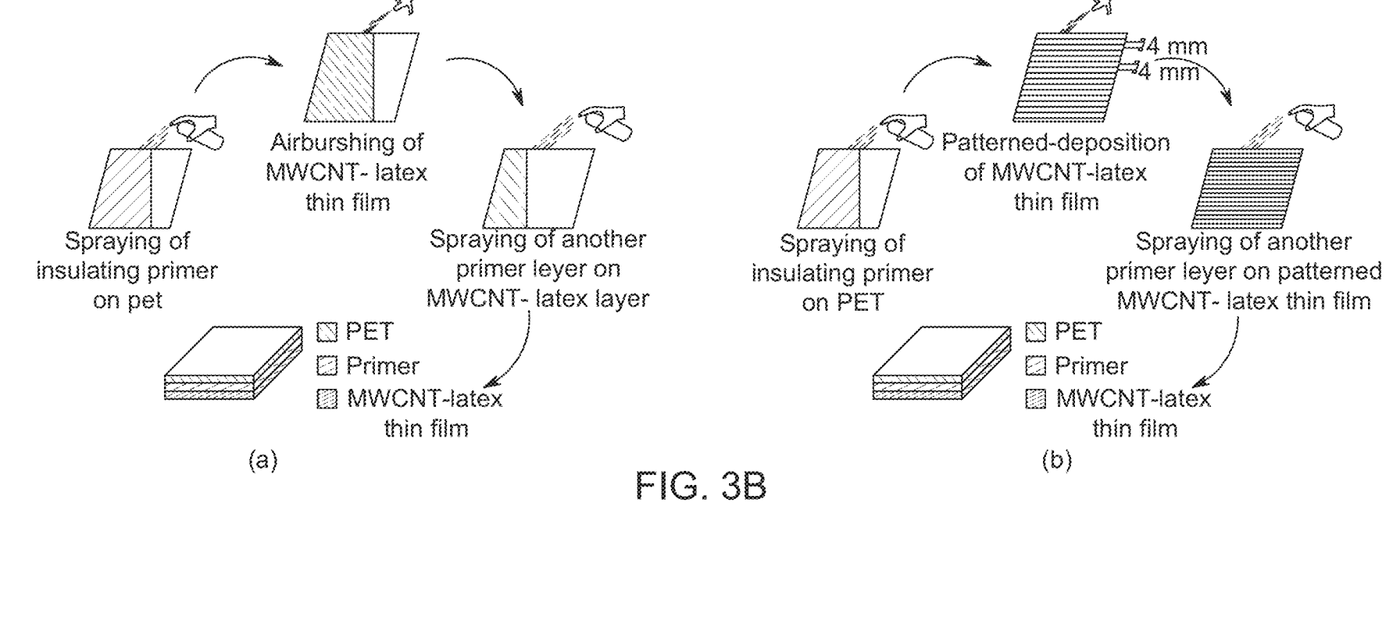
FIG. 3B illustrates processes to fabricate thin film sensors according to one particular embodiment.

The stress sensitive material may include one or more layers. One of the one or more layers may include an insulating primer, such that the insulating primer layer may be deposited between and directly in contact with two stress-sensitive material layers. In some embodiments, the one or more layers may be otherwise arranged. The insulating primer may be biocompatible with the stress-sensitive material. The insulating primer may be composed of resin, solvent, additives, plastic, or other materials. The one or more layers may be deposited onto the object of interest using any of a number of techniques. For example, the layers may sprayed, as shown in FIGS. 3A and 3B, brushed, deposited, or otherwise applied to an object of interest. The material may be applied uniformly across the surface of the object of interest, as shown in FIG. 3A and portion (a) of FIG. 3B, in a pattern, as shown in portion (b) of FIG. 3B, partially applied to the object of interest, or otherwise applied.

The stress-sensitive material may be comprised of one or more solutions. In general, the one or more solutions may include, for example, polyaniline (PANI) emeraldine base, N—N dimethyl formalhyde (DMF), deionized (DI) water, multi-walled carbon nanotubes (MWCNT), poly(sodium 4-styrenesulfonate) (PSS), latex, other elements, compounds, or solutions, or any combination of these materials. For example, one of the one or more solutions may include a PANI solution.

In one example, The solution was prepared by dissolving a polyaniline emeraldine base into a N—N DMF solution at a concentration of around 10 mg/mL. This solution was stirred for about 24 hours with a magnetic stirrer to dissolve the PANI in the DMF. This stirred solution was then vacuum-filtered (using around 0.45 µm pore-size membrane filter) to remove undissolved particles. This filtered solution was diluted around 10-fold by adding appropriate amounts of DI water. The pH of this diluted solution was maintained to be between around 2.5 to around 2.6 using around 10% volume hydrochloric acid.

In one example, one of the one or more solutions may include a carbon nanotube ink prepared by dispersing MWCNT in 2 wt. % PSS solution (in DI). The MWCNTs may be dispersed in PSS solution by ultrasonication to achieve a stable and well-dispersed suspension. This MWCNT-PSS ink may be mixed with PANI in equal proportions (by volume), followed by adding Kynar Aquatec© latex (i.e., the binder), to form a MWCNT-PANI/latex ink. In some embodiments, one of the one or more solutions may include MWCNT dispersed by means of ultrasonication in 2 wt. % PSS solution. A sprayable ink may be produced by adding an appropriate amount of Kynar Aquatec© latex solution with the dispersed MWCNT-PSS solution, which can be sprayed using an airbrush.

At operation 104, the object of interest with the applied stress-sensitive material may be incorporated into a region of interest. The region of interest may be adapted to receive the object of interest with the applied stress-sensitive material. In some embodiments, the object of interest may be the remaining part of the region of interest. For example, the object of interest with the applied stress-sensitive material may be a part of a prosthesis and the region of interest may be remaining extremity of an amputated limb configured to receive the part of the prosthesis via surgery or otherwise. In one example, the object of interest with the applied stress-sensitive material may be a pin on the prosthesis and the region of interest may be a socket configured to receive the pin when the prosthesis is applied to the extremity.

At operation 106, the region of interest with the applied stress-sensitive material may be inserted into an ECT device and the ECT device used to interrogate the region of interest. Interrogation may occur by applying a voltage signal to the electrodes, as described herein. Other imaging devices may be used that are sensitive to electric fields. Electrical capacitance tomography is a soft field imaging technique through which permittivity distribution inside a predefined sensing domain can be reconstructed from capacitance measurements at the boundary electrodes. During ECT interrogation, each electrode may be separately used for exciting the sensing domain with a time-varying electric field, while others may be grounded. Mutual capacitance between pairs of excitation and grounded electrodes may be measured simultaneously, as in portion (b) of FIG. 2B. Then, capacitance data may be used as inputs for solving an inverse problem to reconstruct the permittivity distribution of the sensing domain. In order to reconstruct images from ECT information two problems may need to be solved. The forward problem may solve a system of linear equations to calculate the boundary capacitance responses from a priori knowledge of the permittivity distribution, boundary conditions, and sensing domain geometry. The inverse problem may reconstruct the permittivity distribution of the sensing domain from the measured set of boundary capacitance responses. The formulations of forward and inverse problems is described herein.

In general, the ECT algorithm comprises of the forward and inverse problems. The forward problem may calculate the capacitance response at the boundary electrodes given a known electrical field excitation and spatial permittivity distribution of the sensing region. In contrast, the inverse problem may seek to reconstruct the sensing region's permittivity distribution using the set of boundary capacitance measurements when the sensing region is interrogated using different patterns of applied electrical fields.

The forward problem may be solved in order to calculate the boundary capacitance response when the permittivity distribution inside the sensing domain ($\Omega$) is known. Solving the forward problem may allow calculation of the capacitance between the excitation and sensing electrodes. The ECT forward problem may be governed by the 2D Laplace's equation with electrostatic approximation and steady-state electrical conditions inside $\Omega$:

$$\nabla \cdot (\varepsilon \nabla u) = 0 \quad (1)$$

where $\varepsilon$ and $u$ are the electrical permittivity and electric potential distributions inside $\Omega$, respectively. This second-order partial differential equation may be solved with appropriate boundary conditions as described in Eq. (2) so as to estimate the potential distribution everywhere in $\Omega$. The finite element method (FEM) may be adopted to solve Eq. (1). The corresponding weak-form of the ECT forward problem may be derived by multiplying Eq. (1) with sufficiently smooth test function, $v$, and then integrating over $\Omega$.

$$\int_\Omega v \nabla \cdot (\varepsilon \nabla u) = 0 \quad (2)$$

The inverse problem may be employed for reconstructing the permittivity distribution of $\Omega$ using the set of experimental capacitance measurements at the boundary electrodes due to different boundary electrical field excitations. A Gauss-Newton iterative algorithm may be implemented to minimize the error between computationally obtained (Cc) and experimental capacitance measurements (Cm). The inverse problem may start with an initial assumed permittivity distribution. It should be clarified that Cc may be found by solving the forward problem using the assumed permittivity distribution of $\Omega$.

An error vector (e=Cm−Cc) may then be calculated. This process may be repeated in its entirety until the error ratio $e_r$ (i.e., norm of the error vector to the norm of the measured capacitance) falls below the threshold limit of 0.05%. The ECT inverse problem may be non-linear and ill-posed by nature, and proper regularization should be adopted to ensure smooth convergence of the inverse algorithm. In various embodiments, a Tikhonov regularization technique may be implemented.

Figure 2A:
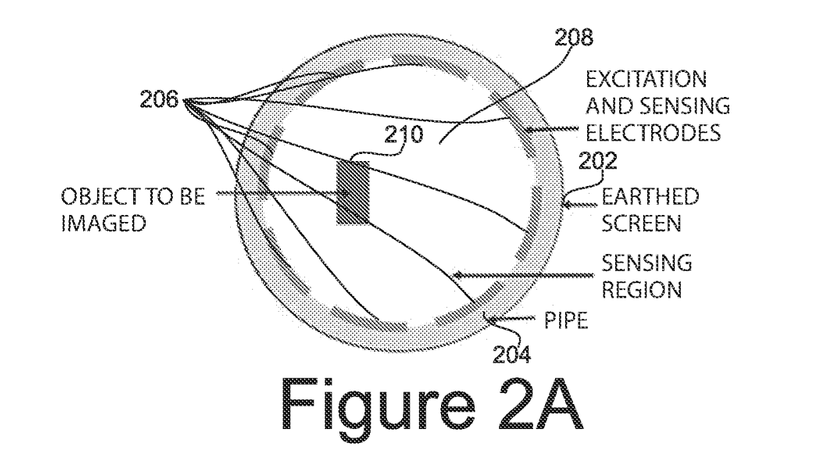
FIG. 2A illustrates an ECT device with an object to be imaged according to one particular embodiment.
Figure 2B:
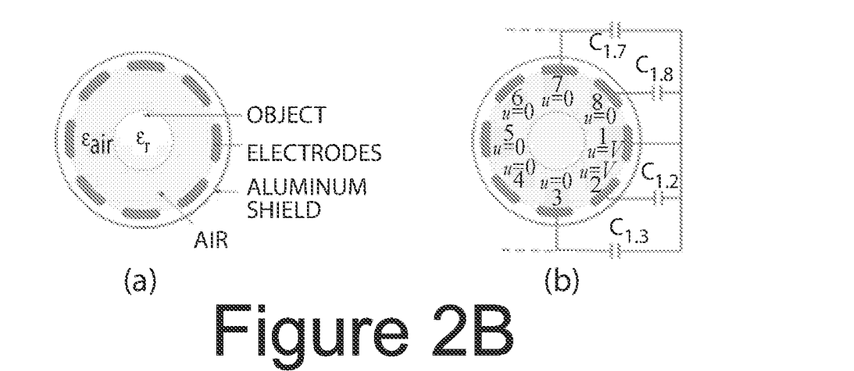
FIG. 2B illustrates an ECT device according to one particular embodiment.
Figure 2C:
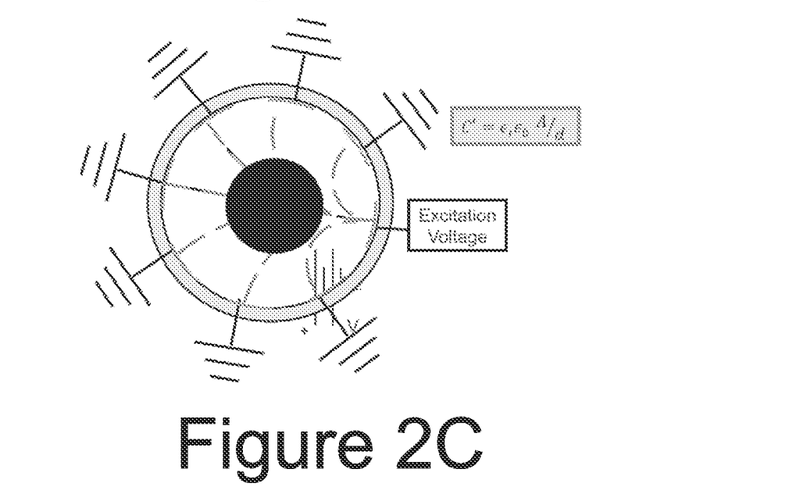
FIG. 2C illustrates an ECT device according to one particular embodiment.

The ECT device, as shown in the example of FIGS. 2A, 2B, and 2C may be configured in a circular shape with an electrode array mounted around the perimeter. In other embodiments, the ECT device may have other geometries or shapes. FIG. 2A illustrates an example ECT device with an object to be imaged according to one particular embodiment. Object 210 may be placed within ECT device 200. Excitation and sensing electrodes 206 may be configured as a circular ring or track in some embodiments. The electrodes may be otherwise arranged to conform to the shape and structure of the ECT device. Low amplitude electric fields can be injected between excitation and sensing electrodes 206 mounted on pipe 204. As a result, the electric field may then interact with the object 210. The raw data collected can be fed as input to an ECT algorithm to back calculate spatial permittivity maps that describe the electrical properties of the cross-section interrogated by the ECT system.

Changes in material (e.g., electrical) properties due to infection or other stressors will be clearly illuminated via the reconstructed electrical images of the cross-section. Additionally, the ECT device may also permit the identification of shapes, sizes, and locations of features of interest within the region of interest. For example, the ECT device may be able to distinguish human tissue, a prosthesis, and an infected region from each other, further allowing for detailed identification and information about any possible changes occurring at the region of interest. As a result, the ECT device can be used to apply medical imaging properties to determine the electrical or dielectric properties of objects of interest implanted within a region of interest. In one example, the ECT device can be used for monitoring deformations or changes in structures, such as pins, sockets, hulls, pipes, beams, or other structures.

FIG. 2B illustrates an ECT device according to one particular embodiment. The ECT device may include a sensing region that may be defined by a set of non-contact electrodes arranged in a typically circular array, similar to FIG. 2A. An alternating current electrical excitation may be applied at one electrode, while the remaining electrodes are grounded, such as the example illustrated in portion (b) of FIG. 2B. In doing so, an electrical field may be propagated between the excitation and all other sensing electrodes. By applying a voltage signal to one of the electrodes and setting the others as ground, an electric field is allowed to propagate through $\Omega$ as depicted in portion (b) of FIG. 2B.

FIG. 2C illustrates an ECT device according to one particular embodiment. In some embodiments, FIG. 2C may be substantially the same as FIGS. 2A and 2B.

Referring back to FIG. 1, at operation 108, the data obtained during interrogation of the region of interest may be used to generate a first map. A series of cross-sections of the region of interest may be captured by the system and a map generated for each cross-section. The first map may be one or more of a spatial permittivity map, a graph, a chart, or other representations of data. This first map can be stored and retained as a reference point indicating a map for the object of interest in the region of interest in its newly implanted condition—before stressors have had the opportunity to materially impact the object of interest.

The ECT device may also be used on objects of interest that do not have a stress-sensitive material. For example, a plastic rod may be used as an object of interest. The plastic rod may be subject to uniaxial and bending loads, while dielectric property changes due to deformation may be monitored with ECT. A load frame may be customized to apply different types of loads (e.g., uniaxial compression and bending) on the plastic rod. Rotary tables and four-jaw adjustable chucks may be used to apply force to the plastic rod. The plastic rod may be fitted into the load frame through the four-jaw-chuck such that the plastic rod is fixed at one end and free at the other. The rod may be placed into the ECT electrode array, such that the rod is located at the middle of the ECT electrode array. A set of baseline capacitance measurement may be obtained and the corresponding permittivity distribution (i.e., baseline) may be reconstructed from the measured set of data. Change in permittivity distributions with respect to the baseline due to the application of loads may or may not occur.

A battery of tests may be applied to the object of interest with the applied stress-sensitive material, such that maps corresponding to each test may be generated. The maps may be used to compare against subsequent changes to the object of interest with the applied stress-sensitive material, therefore, the approximate changes to the object of interest with the applied stress-sensitive material may be estimated. In some embodiments, a battery of tests may not be appropriate and the object of interest with the applied stress-sensitive material may be incorporated directly into the region of interest. The battery of tests may also be applied to the object of interest that does not have stress-sensitive material.

At operation 110, operations 106 and 108 may be repeated after a first length of time to generate a second map. For example, after the device has been implanted or used for a period of time, new measurements can be made and maps generated to depict the characteristics of the region of interest. At operation 112, the first map may be compared to the second map to determine any changes to the region of interest. Operations 110 and 112 may continue to be repeated such that subsequent measurements and comparisons can be repeated at various points in time to measure the region of interest overtime. Maps generated can be compared with each other to identify changes over time or to identify stresses that may have occurred. For example, subsequent maps can be compared back to the baseline or reference map and changes can be studied to determine whether there are any issues with the object of interest, the region of interest, or both. In some embodiments, the maps can be compared visually by an operator while in other embodiments the comparison can be performed by or assisted by automated image processing techniques that can be used to compare the maps and output any changes.

In some embodiments, if the first map is different from a subsequent map, the differences may suggest that the incorporation of the object of interest with the applied stress-sensitive material into the region of interest may not have been successful. In one embodiment, the differences may inform a healthcare practitioner that adjustments to the object of interest may be needed.

The differences may indicate how a stressor has affected the object of interest with the applied stress-sensitive material. For example, a stress-sensitive material sensitive to pH may have been applied to the object of interest which was incorporated into a region of interest. Comparing a second map to a first map of the region of interest may indicate changes, such that the pH of the area surrounding, or on, the object of interest with the applied stress-sensitive material has become more basic. The higher pH may indicate an infection on, or around, the object of interest with the applied stress-sensitive material. A lower pH may indicate an infection as well. The differences may indicate unsuccessful incorporation of the object of interest with the applied stress-sensitive material into the region of interest, such that the object of interest with the applied stress-sensitive material should be removed. In some embodiments, the region of interest or object of interest with the applied stress-sensitive material may be treated or otherwise modified to return the object of interest with the applied stress-sensitive material to the same pH levels represented in the first map.

In some embodiments, if the first map is the same as the second map, the similarity may indicate successful incorporation of the object of interest with the applied stress-sensitive material into the region of interest. The region of interest may continue to be monitored.

FIG. 3A illustrates a spray coated film arranged to form a parallel-plate capacitor according to one particular embodiment. In order to enhance infection detection sensitivity, a pH-sensitive thin film may be fabricated using carbon nanotubes (CNT) and PANI and then applied onto an object of interest. By way of example, a diluted and pH-adjusted PANI solution with a dispersed CNT solution may be created so that non-composite thin film pH sensors can be fabricated by spray-painting it onto any surface. MWCNT may be dispersed in 2 wt % PSS solution by ultrasonication. The PANI solution and the dispersed MWCNT-PSS solution may be mixed together in equal proportions. This may be followed by adding an appropriate amount of latex solution to form a sprayable MWCNT-based ink. An airbrush may then be employed to spray the MWCNT-based ink onto objects of interest, such as glass slides, plastic rods, beams, prostheses, or other structures. The air-dried films (referred to as MWCNT-PANI/latex nanocomposites) may then be employed as sensors, or stress-sensitive materials. However, any type of brush or spraying method known by a person of ordinary skill in the art may be used to distribute the MWCNT onto the structures.

Because the MWCNT-PANI/latex nanocomposites are sensitive to different stressors, the MWCNT-PANI/latex nanocomposites can be used with the ECT device for mapping an object of interest to monitor changes to the object of interest with the applied stress-sensitive material. Thus, the MWCNT-PANI/latex nanocomposites can be applied to objects of interest for monitoring changes due to various stressors, such as pH or strain.

For example, a pH-sensitive thin film may be fabricated using MWCNT and PANI. The thin film's pH sensitivity may be characterized by exposing it to different pH buffer solutions and measuring its corresponding dielectric property changes. A circular plastic rod may be used as a phantom for a human prosthesis, for example, to simulate the portion of an artificial limb that would be embedded in and bonded to the human body. The thin film may be deposited onto the surface of the prosthetic phantom and exposed to different pH buffer solutions. The ECT system may be used to interrogate the prosthetic phantom placed in the sensing area.

As illustrated, FIG. 3A may illustrate that the film, glass slides, and aluminum tape electrodes can be arranged to from a parallel plate capacitor test set-up. An alternating current signal may be injected, thus allowing the system's current response to be recorded. The system may detect changes in permittivity due to different pH buffers, and the reconstructed permittivity maps may identify the location of the permittivity changes, as well as the location of the prosthesis itself. The ECT device with a pH-sensitive thin film can be used to effectively image and detect properties of dielectric properties of human tissues to monitor skin and tissue infections.

FIG. 3B illustrates processes to fabricate thin film sensors according to one particular embodiment. In some embodiments, spray coating techniques may be adopted to fabricate strain-sensitive nanocomposite thin films. For example, MWCNT may be dispersed by means of ultrasonication in about 2 wt. % PSS solution. A sprayable ink may be produced by adding an appropriate amount of Kynar Aquatec© latex solution with the dispersed MWCNT-PSS solution, which can be sprayed using an airbrush as used in this work. The MWCNT-latex thin film can be spray coated onto different types structural surfaces and it can serve as a distributed strain sensor. In one embodiment, the thin films may be deposited on the transparent Polyethylene terephthalate (PET) sheet and specimens may be made for their strain sensitivity characterization. For example, the nanocomposite thin film can be increased by changing the deposition patterns of MWCNT-latex thin film and the insulating primer. In one example, a layer of insulating paint primer may be deposited onto a PET sheet. A separate layer of MWCNT-latex thin film may be deposited onto the primer surface by airbrushing. Another layer of insulating primer may be deposited on the top of the MWCNT-latex thin film, as shown in portion (a) of FIG. 3B.

In one example, the fabrication of a thin film, as shown in portion (b) of FIG. 3B, may be started by depositing a layer of insulating primer on the top of a PET sheet. Blue masking tapes of about 4 millimeter thickness, may be fixed onto primer-coated surface for patterned deposition of the MWCNT-latex ink. The tape may be fixed so the distance between two consecutive parallel tapes may be about 4 millimeters. A layer of MWCNT-latex thin film may be airbrushed on the masked surface of primer-coated PET. The masking tapes may be removed and another layer of primer may be spray coated on the top of the final surface. Alternative layers of conductive MWCNT-latex thin film and insulating primer may serve as a compound parallel plate capacitor. The strain sensing response of the nanocomposite thin film may be enhanced as a result. The fabrication process may be accomplished using robotic spray fabrication tools for covering structural surfaces. In some embodiments, the thin film may be fabricated with different material using a different process.

Figure 4A:
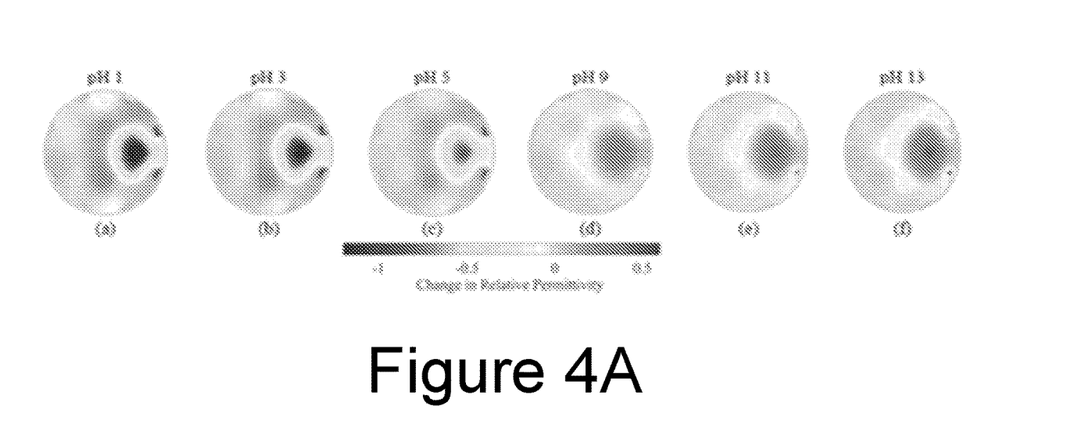
FIG. 4A illustrates spatial permittivity maps of a prosthesis coated with pH sensitive film according to one particular embodiment.

FIG. 4A illustrates spatial permittivity maps of a prosthesis coated with pH sensitive film according to one particular embodiment. For example, a plastic rod may be used as a human prosthesis coated with a pH-sensitive nanocomposite film subject to ECT testing. Monitoring for infection occurring at the prosthesis interface may involve two aspects. The first may be the use of a pH-sensitive MWCNT-PANI/latex thin film, which could be applied at the human-prosthesis interface for monitoring pH changes resulting from infection. The fabrication process for the pH-sensitive MWCNT-PANI/latex thin film may be described in greater detail herein and may be shown in FIG. 3A. The second is the implementation of a soft field imaging technique based on the electrical capacitance tomography algorithm, which may use boundary electrical field excitations and capacitance measurements for reconstructing the spatial permittivity of the sensing area enclosed by an array of electrodes arranged in a circular pattern. The device may be an ECT device, as shown in FIGS. 2A, 2B, and 2C, or another imaging device.

Referring back to FIG. 4A, the maps (portions (a)-(f)) indicate the object of interest with the applied stress-sensitive material was exposed to environment conditions with a pH of 9, 11, and 13, which may be infection conditions. For example, the permittivity map, or distribution, corresponding to the pH 7 case may be a baseline. The baseline may be subtracted from all other permittivity distributions (for other pH cases). The permittivity of the region of interest corresponding to where the object of interest with the applied stress-sensitive material was located may increase as the prosthesis is exposed to more alkaline pH buffer solutions.

Figure 4B:
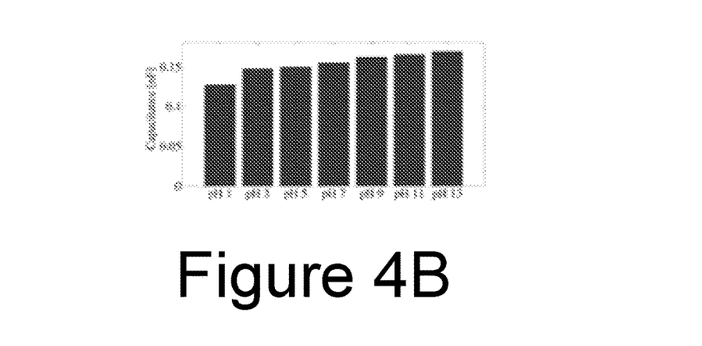
FIG. 4B illustrates a graph comparing capacitance to pH values according to one particular embodiment.

FIG. 4B illustrates a graph comparing capacitance to pH values according to one particular embodiment. The stress-sensitive material may change in properties in reaction to stressors. For example, the capacitance of the stress-sensitive material increased as the pH increased. The capacitance may increase as a result in the change of a dielectric property of the stress-sensitive material.

Figure 5A:
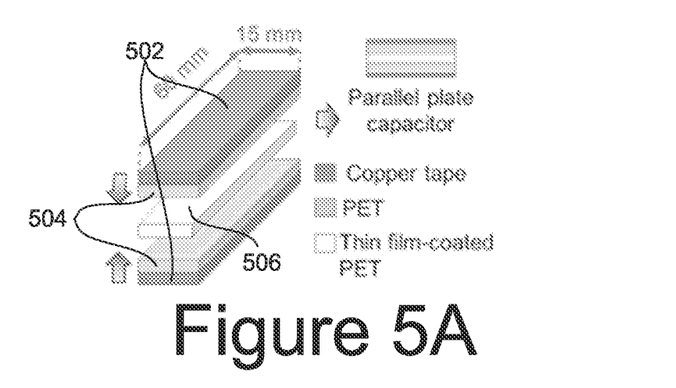
FIG. 5A illustrates a thin film-contained parallel plate capacitor subject to ECT testing according to one particular embodiment.

FIG. 5A illustrates a thin film-contained parallel plate capacitor subject to ECT testing according to one particular embodiment. The thin film may be fabricated in a way described herein, such as shown in FIG. 3B. For example, the thin films may be cut into proper sizes and assembled to form a parallel plate capacitor sensitive to strain. Thin film-coated PET 506 may be cut into a strip and put into a load frame. Adhesive copper tape 502 may be affixed on a side of pristine PET strips 504 of similar size, and attached on both sides of thin film-coated PET strip 506 which was clamped to a load frame. Such arrangement of thin film-coated PET 506, copper tape 502, and PET strips 504 may form a parallel plate capacitor with thin film as dielectric medium between two parallel electrodes (not shown). The electrodes (not shown) may be externally attached to prevent deformation while thin film-coated PET 506 is subjected to load. Uniaxial tensile strain may be applied to the parallel plate capacitor. The capacitances of the parallel plate capacitors made from stress-sensitive material may be measured.

Figure 5B:
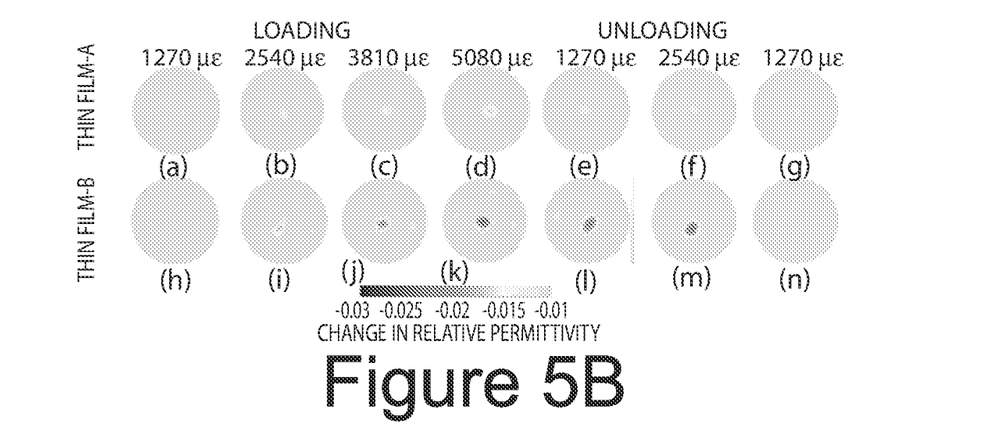
FIG. 5B illustrates spatial permittivity maps of a thin film-contained parallel plate capacitor according to one particular embodiment.

FIG. 5B illustrates spatial permittivity maps of a thin film-contained parallel plate capacitor according to one particular embodiment. In one example, the strain sensitivity of a first thin film (portions (a)-(g) of FIG. 5B) may be lower than that of a second thin film (portions (h)-(n) of FIG. 5B). The signal-to-noise ratio may be higher (i.e. the magnitude of the change in electrical permittivity is larger) for the second thin film when subjected to uniaxial loading and unloading than the first thin film. The first thin film may be applied evenly to an object of interest and the second thin film may be applied in a pattern to an object of interest. The first thin film may be fabricated in a process similar to that shown in portion (a) of FIG. 3B and the second thin film may be fabricated in a process similar to that shown in portion (b) of FIG. 3B.

Figure 5C:
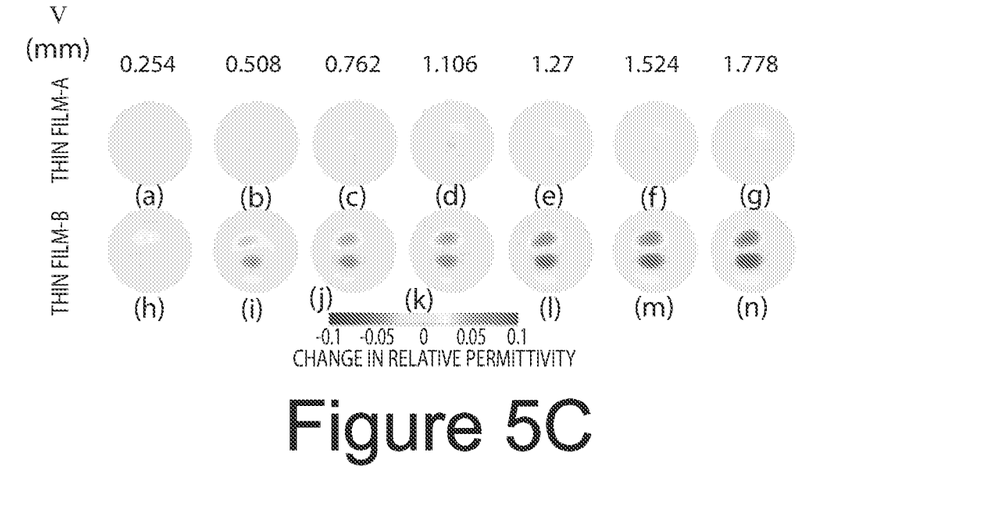
FIG. 5C illustrates spatial permittivity maps of a thin film-contained parallel plate capacitor according to one particular embodiment.

FIG. 5C illustrates spatial permittivity maps of a thin film-contained parallel plate capacitor according to one particular embodiment. In one example, the strain sensitivity of a first thin film (portions (a)-(g) of FIG. 5B) may be lower than that of a second thin film (portions (h)-(n) of FIG. 5B). The signal-to-noise ratio may be higher (i.e. the magnitude of the change in electrical permittivity is larger) for the second thin film when subjected to uniaxial loading and unloading than the first thin film. A bipolar change in electrical permittivity may occur on the second thin film. The first thin film may be applied evenly to an object of interest and the second thin film may be applied in a pattern to an object of interest. The first thin film may be fabricated in a process similar to that shown in portion (a) of FIG. 3B and the second thin film may be fabricated in a process similar to that shown in portion (b) of FIG. 3B.

Figure 6A:
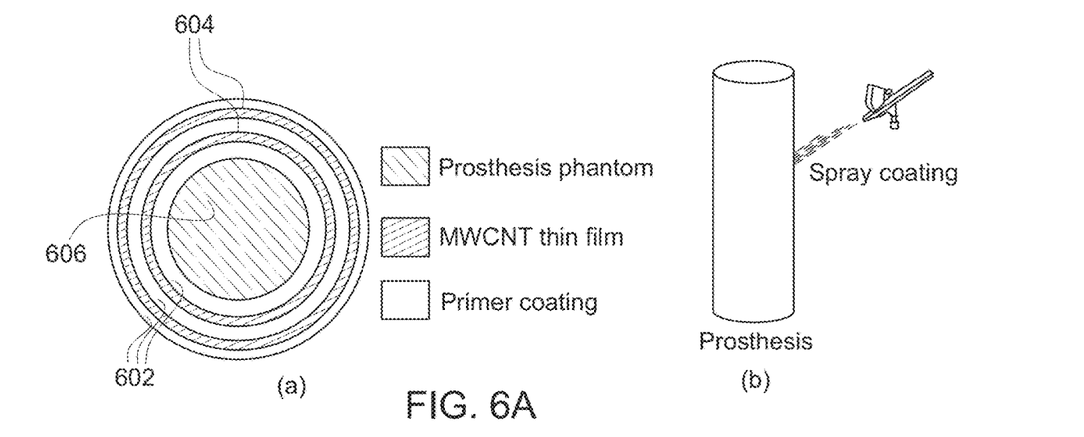
FIG. 6A illustrates a rod used as a human prosthesis coated with a strain-sensitive nanocomposite film subject to ECT testing according to one particular embodiment.

FIG. 6A illustrates a rod used as a human prosthesis coated with a strain-sensitive nanocomposite film subject to ECT testing according to one particular embodiment. The strain-sensitive nanocomposite film may be applied through various methods. For example, a layer of insulating paint primer 602 may be deposited onto prosthesis phantom 606. MWCNT-latex thin film 604 may be spray coated multiple time to form a ring of layers, as shown in FIG. 6A. Other processes, such as those described herein, may be used.

The film used may have a permittivity that is sensitive to applied strains. The nanocomposite physically represents a multilayered structure with alternating layers of MWCNT-latex thin films 604 and insulating paint primer 602, as shown in portion (a) of FIG. 6A. When the object of interest is loaded, the multilayered MWCNT-latex thin film 604 (which represents stacked parallel-plate capacitors) may change its thickness due to Poisson's effect, which in turn may cause the dielectric properties or the perceived permittivity of the system to change.

In one example, a tissue-bone-prosthesis surrogate may be used. The tissue-bone-prosthesis surrogate may include a sawbone femur, an aluminum rod, water-saturated foam, stress-sensitive material, and other materials. The tissue-bone-prosthesis surrogate may be interrogated.

Figure 6B:
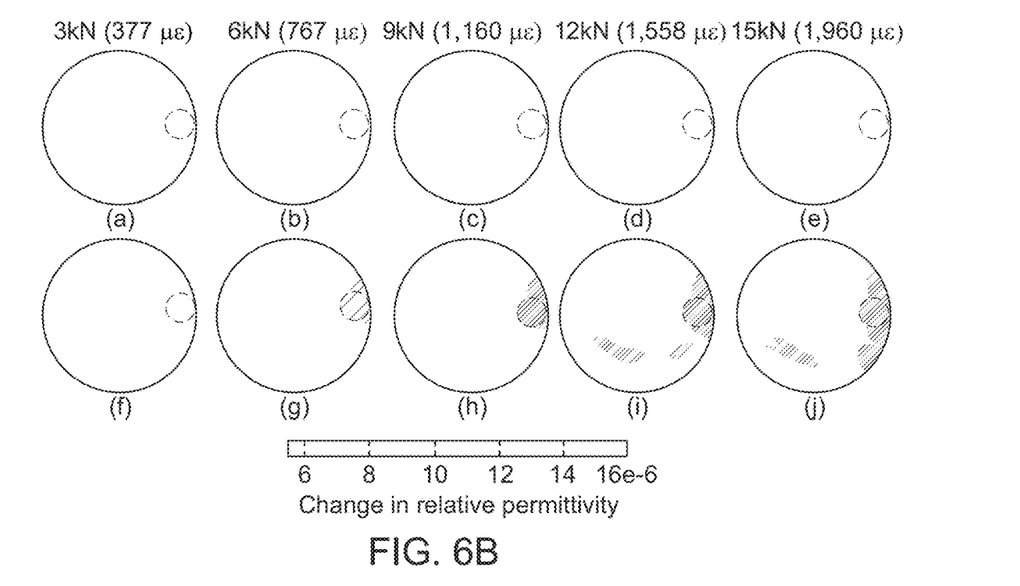
FIG. 6B illustrates spatial permittivity maps of a strain sensitive film according to one particular embodiment.

FIG. 6B illustrates spatial permittivity maps of a strain sensitive film according to one particular embodiment. Portions (a)-(e) may show the reconstructed spatial permittivity maps of the entire sensing domain for a pristine rod (without a stress-sensitive material) subject to different magnitudes of tensile strains. Note that these ECT results may be changes in permittivity relative to the permittivity distribution of the unloaded prosthesis phantom in air; hence, the rod itself may not be shown.

Portions (f)-(j) may show the reconstructed spatial permittivity maps of the entire sensing domain for a film-coated prosthesis phantom (with an applied strain-sensitive material) subject to different magnitudes of tensile strains. The film-coated prosthesis phantom may be similar to the one in FIG. 6A. The ECT results for the film-coated prosthesis phantom may show strain-induced permittivity changes. The location of these permittivity changes may correspond to where the film-coated prosthesis phantom was physically in the sensing domain.

Figure 6C:
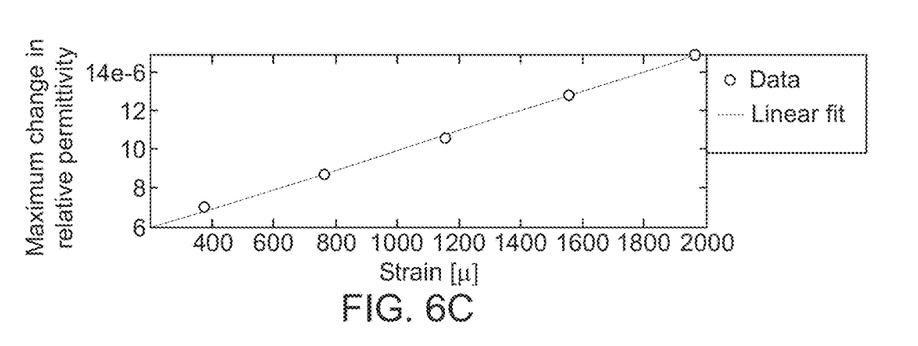
FIG. 6C illustrates a graph of a strain sensitive film comparing change in relative permittivity to strain according to one particular embodiment.

FIG. 6C illustrates a graph of a strain sensitive film comparing change in relative permittivity to strain according to one particular embodiment. The data used for the graph may be a result of the system described in FIG. 6A. The maximum change in permittivity was obtained at each strain state which may indicate the linear dependence of permittivity with respect to strain.

Figure 7:
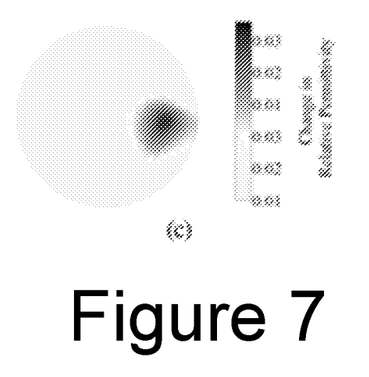
FIG. 7 illustrates a spatial permittivity map of a prosthesis phantom subject to ECT testing according to one particular embodiment.

FIG. 7 illustrates a spatial permittivity map of a prosthesis phantom subject to ECT testing according to one particular embodiment. The prosthesis phantom may include a lamb shank and a rod. The spatial permittivity map may indicate the position and relative permittivity of the prosthesis phantom within a sensing area of an ECT device, as shown in FIGS. 2A, 2B, and 2C.

Figure 8A:
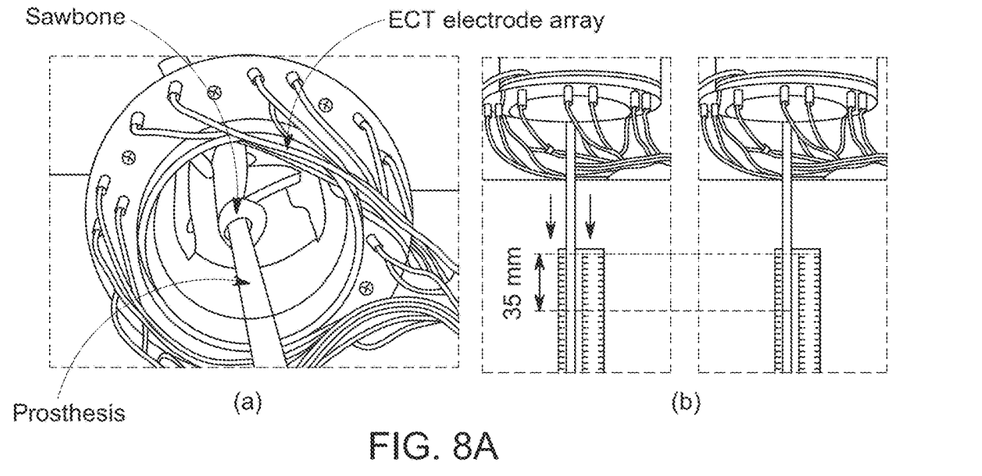
FIG. 8A illustrates a rod used as a bone-prosthesis phantom subject to ECT testing as the rod was pulled out from within the bone according to one particular embodiment.

FIG. 8A illustrates a rod used as a bone-prosthesis phantom subject to ECT testing as the rod was pulled out from within the bone according to one particular embodiment. The object of interest may simulate an osseointergrated prosthesis (01P) surrogate. The OIP surrogate may include a poly(vinyl chloride) (PVC) rod, a femur sawbone, and other materials. An ECT device may be used to interrogate the OIP surrogate as shown in portion (a) of FIG. 8A. As shown in portion (b) of FIG. 8A, the rod may be gradually pulled out from the femur sawbone starting from around 0 mm to around 35 mm. At the end of each 5 mm movement, the system may have been interrogated by the ECT system, and the corresponding electrical permittivity distributions may have been reconstructed from the measured set of boundary capacitance responses, as shown in FIG. 8D.

Figure 8B:
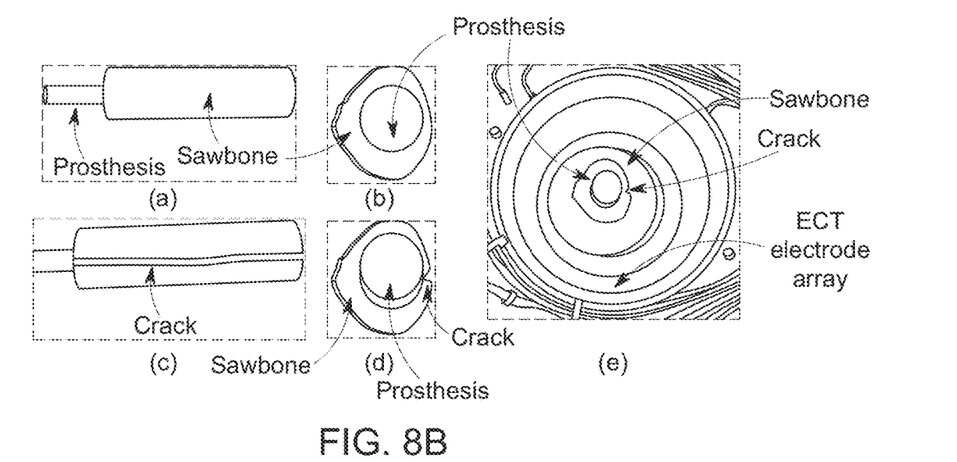
FIG. 8B illustrates a rod used as a bone-prosthesis phantom subject to ECT testing according to one particular embodiment.

FIG. 8B illustrates a rod used as a bone-prosthesis phantom subject to ECT testing according to one particular embodiment. Prosthesis loosening, if undetected at an early stage, can cause stress concentrations in bone and, ultimately, cracks (or fracture) can propagate at the bone-prosthesis interface, thereby leading to OIP failure and extreme pain for an amputee. Similar to the surrogate described above, a sawbone femur may be included in the OIP surrogate. The OIP surrogate may further include an aluminum rod, epoxy, or other materials. A slit, or crack, may be cut along the side and in the direction of the longitudinal axis of the femur, as shown in portions (c) and (d) of FIG. 8B. The surrogate may be interrogated by an ECT device, as described herein.

Figure 8C:
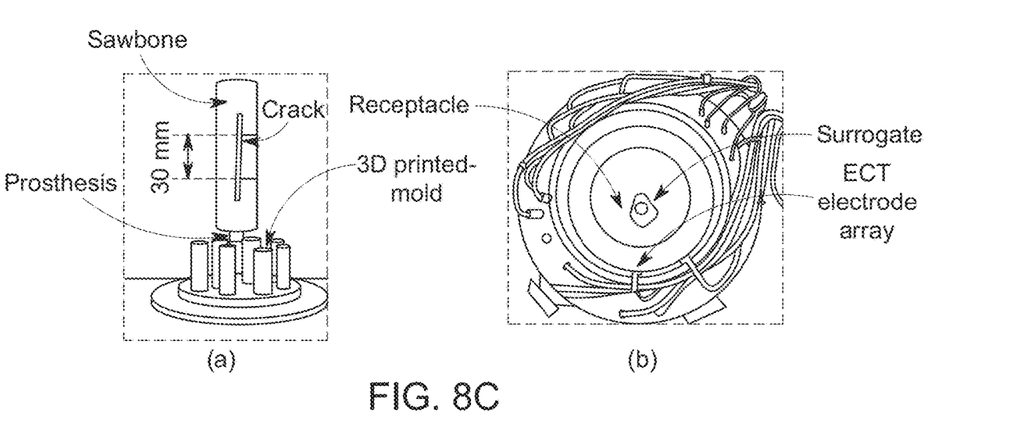
FIG. 8C illustrates a rod used as a bone-prosthesis phantom subject to ECT testing where the bone has a crack according to one particular embodiment.

FIG. 8C illustrates a rod used as a bone-prosthesis phantom subject to ECT testing where the bone has a crack according to one particular embodiment. The bone-prosthesis phantom may be similar to the one shown in FIGS. 8A and 8B. Portion (a) of FIG. 8C may illustrate a printed mold that may be used to hold the bone-prosthesis phantom in an ECT device. Portion (a) may illustrate a crack on the bone-prosthesis phantom. Portion (b) of FIG. 8C illustrates the bone-prosthesis phantom within an ECT device, as described herein.

Figure 8D:
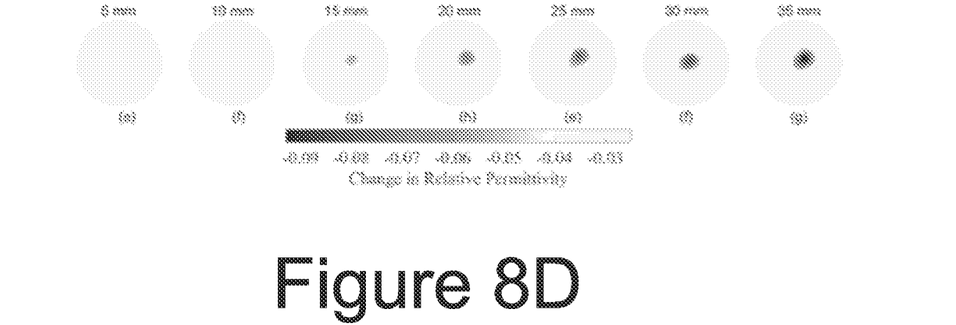
FIG. 8D illustrates spatial permittivity maps of a bone-prosthesis, as a rod is loosened according to one particular embodiment.

FIG. 8D illustrates spatial permittivity maps of a bone-prosthesis, as a rod is loosened according to one particular embodiment. The spatial permittivity maps illustrate different measurement taken as a rod within a bone-prosthesis phantom, as shown in FIGS. 8A, 8B, and 8C, may have been removed from the bone-prosthesis phantom at around 5 millimeters, around 10 millimeters, around 15 millimeters, around 20 millimeters, around 25 millimeters, around 30 millimeters, and around 35 millimeters. The measurements may have been compared against a baseline (e.g., no loosening or removal) to generate the permittivity maps of FIG. 8D.

Figure 8E:
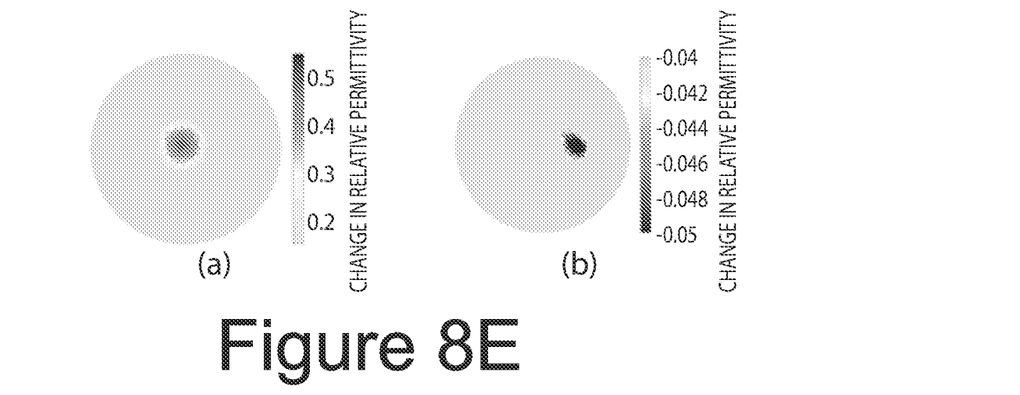
FIG. 8E illustrates spatial permittivity maps of a bone-prosthesis according to one particular embodiment.

FIG. 8E illustrates spatial permittivity maps of a bone-prosthesis according to one particular embodiment. The spatial permittivity maps illustrate different measurement taken as a fracture, or crack, may have been introduced on a bone-prosthesis phantom, as shown in FIGS. 8A, 8B, and 8C. Portion (a) of FIG. 8E may illustrate a pristine OIP surrogate, while portion (b) of FIG. 8E may illustrate the changes in permittivity distribution due to the crack. The measurement of portion (b) of FIG. 8E may have been compared against a baseline (e.g., no crack in the OIP surrogate) to generate the permittivity map of portion (b) of FIG. 8E.

Figure 8F:
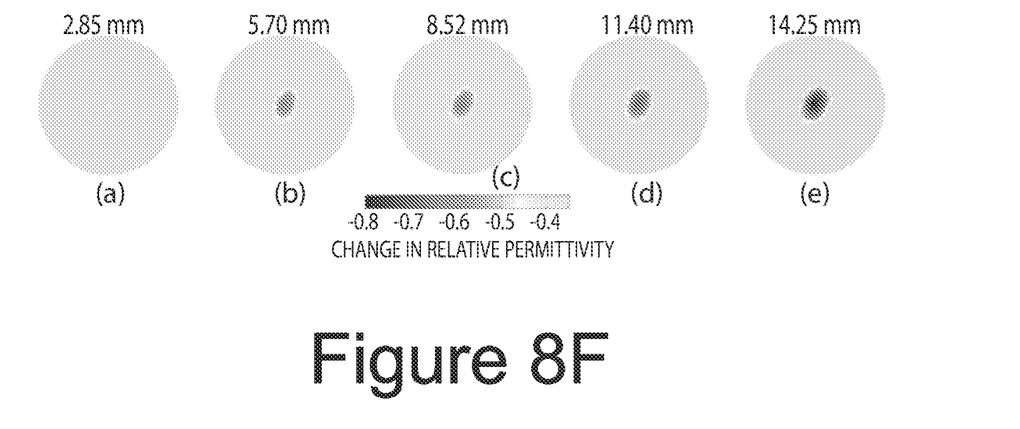
FIG. 8F illustrates spatial permittivity maps of a bone-prosthesis as a crack is introduced to the bone according to one particular embodiment.

FIG. 8F illustrates spatial permittivity maps of a bone-prosthesis as a crack is introduced to the bone according to one particular embodiment. The spatial permittivity maps illustrate different measurement taken as a fracture, or crack, may have been introduced on the longitudinal direction of the OIP surrogate, as shown in FIGS. 8A, 8B, and 8C. The crack may have been introduced in increments of around 2.85 millimeters, around 5.70 millimeters, around 8.52 millimeters, around 11.40 millimeters, and around 14.25 millimeters. The measurements may have been compared against a baseline (e.g., no crack in the OIP surrogate) to generate the permittivity maps of FIG. 8F.

Figure 8G:
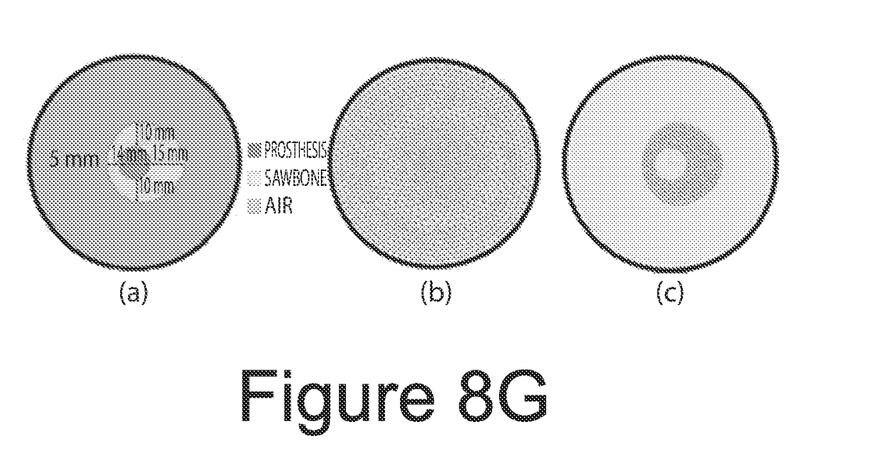
FIG. 8G illustrates a bone-prosthesis surrogate according to one particular embodiment.

FIG. 8G illustrates a bone-prosthesis surrogate according to one particular embodiment. Portion (a) of FIG. 8G may illustrate a diagram of an OIP surrogate in an ECT device. The OIP surrogate may be similar to that shown in FIGS. 8A, 8B, and 8C. The ECT device may be similar to that shown in FIGS. 2A, 2B, and 2C. Various dimensions may be used to describe parts of the OIP surrogate. However, the dimensions of the parts of the OIP surrogate may be different. For example, the prosthesis may be around 14 millimeters. The distance from the prosthesis to a first edge of the sawbone may be around 10 millimeters. The distance from the prosthesis to a second edge of the sawbone may be around 15 millimeters. The distance from the prosthesis to a third edge of the sawbone may be around 10 millimeters. The distance from the prosthesis to a fourth edge of the sawbone may be around 5 millimeters.

Portion (b) of FIG. 8G may illustrate measurements taken of the set-up describe above. For example, the measurement may have been modeled by FEM and discretized using linear triangular elements. FEM may be used to help solve Eq. (1) (the 2D Laplace equation). Portion (c) of FIG. 8G may illustrate elements of portion (b) reconstructed by a limited region tomographic (LRT) image reconstruction algorithm. The main objective of LRT may be to enhance the imaging performance of the inverse algorithm by limiting the reconstruction region to a particular zone where changes in electrical permittivity may be expected to occur. In doing so, the number of unknown image pixels can be significantly reduced with LRT imaging.

Figure 8H:
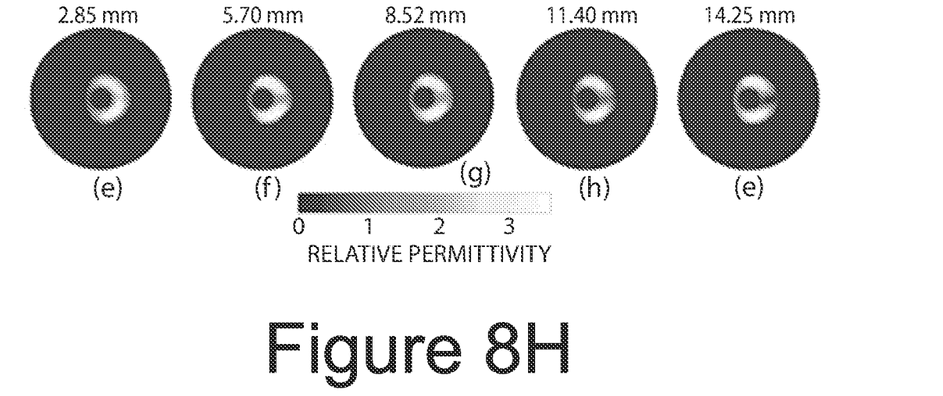
FIG. 8H illustrates spatial permittivity maps of a bone-prosthesis at different crack depths of the bone according to one particular embodiment.

FIG. 8H illustrates spatial permittivity maps of a bone-prosthesis at different crack depths of the bone according to one particular embodiment. The spatial permittivity maps illustrate different measurement taken as a fracture, or crack, may have been introduced on the longitudinal direction of the OIP surrogate, as shown in FIGS. 8A, 8B, and 8C. The crack may have been introduced in increments of around 2.85 millimeters, around 5.70 millimeters, around 8.52 millimeters, around 11.40 millimeters, and around 14.25 millimeters. The measurements may have been compared against a baseline (e.g., no crack in the OIP surrogate) to generate the permittivity maps of FIG. 8H. LRT image reconstruction algorithms may have been used to generate the permittivity maps of FIG. 8H. The spatial permittivity maps, as shown in FIG. 8H, may illustrate gradual shape changes observed near the location of the fracture, which may correspond to the depth of the fracture increasing. The shape of the change in electrical permittivity may resemble the cross-sectional shape of the fracture.

Figure 8I:
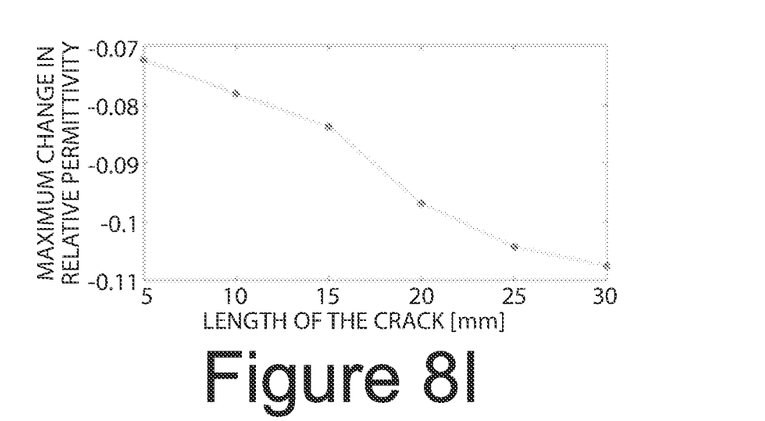
FIG. 8I illustrates a graph of a bone-prosthesis comparing change in relative permittivity to the length of a crack in the bone according to one particular embodiment.

FIG. 8I illustrates a graph of a bone-prosthesis comparing change in relative permittivity to the length of a crack in the bone according to one particular embodiment. The graph may illustrate different measurement taken as a fracture, or crack, may have been introduced on the longitudinal direction of the OIP surrogate, as shown in FIGS. 8A, 8B, and 8C. The maximum change in permittivity was obtained at different crack points. The graph may indicate a decrease in the maximum change of relative permittivity as the length of the crack in the OIP surrogate increases.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A non-contact, non-invasive monitoring system comprising:
    a stress-sensitive film applied to an object of interest;
    an electrical capacitance tomography (ECT) device comprising a sensing region defined by a set of non-contact electrodes to be charged, thereby creating an electric field, wherein the ECT device measures capacitance in the sensing region, and wherein the set of non-contact electrodes are arranged on the ECT device based on a geometry suitable for the object of interest being placed into the ECT device; and
    wherein the electric field of the ECT device interrogates the object of interest having the stress-sensitive film placed within the sensing region.

2. The system of claim 1, wherein the object of interest is a prosthesis.

3. The system of claim 2, wherein the prosthesis is attached to an amputated limb.

4. The system of claim 1, wherein the object of interest is a rotor blade.

5. The system of claim 4, wherein the rotor blade is attached to a rotor.

6. The system of claim 1, wherein the object of interest is a column.

7. The system of claim 6, wherein the column is attached to a structure.

8. The system of claim 1, wherein the object of interest is a cable.

9. The system of claim 8, wherein the cable is attached to a corresponding gap in a longer cable.

10. The system of claim 1, wherein the stress-sensitive film comprises a dielectric property sensitive to strain.

11. The system of claim 1, wherein the stress-sensitive film comprises a dielectric property sensitive to pH.

12. The system of claim 1, wherein the stress-sensitive film comprises one or more of multi-walled carbon nanotubes (MWCNT), polysodium 4-styrenesulfonate, latex, polyaniline emeraldine base, N—N dimethyl-formaldehyde, and deionized water.

13. The system of claim 1, wherein the stress-sensitive film is applied to the object of interest in pattern.

14. The system of claim 1, the stress-sensitive film is applied to the object of interest in layers, such that a stress-sensitive portion of the stress-sensitive film is surrounded on a first side and a second side by insulating primer.

* * * * *